(12) United States Patent
Park

(10) Patent No.: US 9,468,561 B2
(45) Date of Patent: Oct. 18, 2016

(54) MEDICAL DRESSING AND METHOD FOR MAKING THE SAME

(71) Applicants: Ji Hye Park, Yangsan-si (KR); Young Joon Park, Yangsan-si (KR)

(72) Inventor: Ji Hye Park, Yangsan-si (KR)

(73) Assignees: Ji Hye Park (KR); Young Joon Park (KR)

( * ) Notice: Subject to any disclaimer, the term of this patent is extended or adjusted under 35 U.S.C. 154(b) by 538 days.

(21) Appl. No.: 14/016,301

(22) Filed: Sep. 3, 2013

(65) Prior Publication Data

US 2014/0148748 A1 May 29, 2014

(30) Foreign Application Priority Data

Nov. 28, 2012 (KR) .......................... 10-2012-0136331

(51) Int. Cl.
| | |
|---|---|
| *A61L 15/58* | (2006.01) |
| *A61F 13/02* | (2006.01) |
| *B32B 38/00* | (2006.01) |
| B32B 37/26 | (2006.01) |

(52) U.S. Cl.
CPC ....... *A61F 13/0266* (2013.01); *A61F 13/0259* (2013.01); *B32B 38/0004* (2013.01); *B32B 37/26* (2013.01); *B32B 2037/268* (2013.01); *B32B 2556/00* (2013.01); *Y10T 156/1082* (2015.01)

(58) Field of Classification Search
CPC ....... A61L 15/58; A61L 15/60; A61L 15/18; A61L 15/46; A61L 2300/404; A61L 15/44; A61L 15/28; A61F 2013/00748; A61F 13/0203; A61F 13/02
See application file for complete search history.

(56) References Cited

U.S. PATENT DOCUMENTS 6,008,429 A * 12/1999 Ritger ..................... A61F 13/02
 206/441
6,482,491 B1 * 11/2002 Samuelsen .......... A61F 13/0203
 424/448

* cited by examiner

*Primary Examiner* — Ophelia A Hawthorne
(74) *Attorney, Agent, or Firm* — Park & Associates IP Law, P. C.

(57) ABSTRACT

A medical dressing is used to dress and treat skin wounds such as burns, cuts or traumatic injuries, and a method for making the same. The medical dressing includes an auxiliary release paper which makes it convenient to separate a pressure sensitive adhesive sheet from a release paper and is very easily separated from the pressure sensitive adhesive sheet after application to a wound site, thus improving the convenience of use of the dressing, and prevents the contamination of the pressure sensitive adhesive sheet in the process of either separating the pressure sensitive adhesive sheet from the release paper or separating the auxiliary release paper, thus preventing the secondary bacterial infection of a wound site, and is not exposed to the outside so that the dressing has an improved appearance and is convenient to carry and store.

6 Claims, 5 Drawing Sheets

MEDICAL DRESSING AND METHOD FOR MAKING THE SAME

REFERENCE TO RELATED APPLICATIONS

This application claims the priority benefit of Korean Patent Application No. 10-2012-0136331 filed on Nov. 28, 2012, the entire contents of which are incorporated herein by reference.

FIELD OF THE INVENTION

The present invention relates to a medical dressing, which is used to dress and treat skin wounds such as burns, cuts or traumatic injuries, and a method for making the same, and more particularly to a medical dressing comprising an auxiliary release paper which makes it convenient to separate a pressure sensitive adhesive sheet from a release paper and is very easily separated from the pressure sensitive adhesive sheet after application to a wound site, thus improving the convenience of use of the dressing, prevents the contamination of the pressure sensitive adhesive sheet in the process of either separating the pressure sensitive adhesive sheet from the release paper or separating the auxiliary release paper, thus preventing the secondary bacterial infection of a wound site, and is not exposed to the outside so that the dressing has an improved appearance and is convenient to carry and store, and a method for making the medical dressing.

BACKGROUND OF THE INVENTION

Generally, medical dressings are widely used to dress and treat skin wounds such as slight burns, cuts or traumatic injuries. In other words, medical dressings function to reduce the evaporation of heat and the loss of moisture from the wound surface so as to prevent the contamination of the wound and also function to reduce the growth of bacteria in wounds.

Such medical dressings comprise a pressure sensitive adhesive sheet attached to the upper surface of a release paper and provide the above-described functions by separating the pressure sensitive adhesive sheet from the release paper and applying an adhesive surface, provided on the lower surface of the pressure sensitive adhesive sheet, to the wound surface.

However, in the process of separating the pressure sensitive adhesive sheet from the release paper before application to a wound site, the contamination of the pressure sensitive adhesive sheet can occur because the user grips the pressure sensitive adhesive sheet. In addition, because the thickness of the pressure sensitive adhesive sheet tends to decrease gradually, the operation of separating the pressure sensitive adhesive sheet from the release paper is inconvenient, and thus the medical dressing is inconvenient to use. The reason why the thickness of the pressure sensitive adhesive sheet decreases gradually is to further improve the wearing feeling of the pressure sensitive adhesive sheet and the activity of a patient to which the pressure sensitive adhesive sheet is being applied.

Accordingly, in recent years, dressings (i.e., medical bandages) that have a separate release paper between the release paper and the pressure sensitive adhesive sheet in order to facilitate the separation of the pressure sensitive adhesive sheet from the release paper have been reported. For example, Korean Utility Model Registration No. 20-0439156 discloses gripping the grip portion of a separate release paper by fingers, separating a pressure sensitive adhesive sheet from a release paper, and then separating the separate release paper from the pressure sensitive adhesive sheet while applying the pressure sensitive adhesive sheet to a wound site.

According to the configuration disclosed in the above Utility Model document, the pressure sensitive adhesive sheet can be applied to a wound site after gripping the grip portion of the separate release paper by fingers without gripping the pressure sensitive adhesive sheet, and separating the pressure sensitive adhesive sheet from the release paper, and thus secondary bacterial infection of the wound site can be prevented while the dressing is convenient to use. However, the area of a portion of the separate release paper, which is attached to the pressure sensitive adhesive sheet, differs from the area of the grip portion of the separate release paper. Specifically, the grip portion is formed to have a smaller area. Because the area of a portion of the separate release paper, which is attached to the pressure sensitive adhesive sheet, is larger, detachment of the grip portion is detached in the process of gripping the grip portion by fingers and separating the separate release paper frequently occurs.

For this reason, it is not easy to separate the separate release paper from the adhesive paper after gripping the grip portion by fingers, and thus a portion of the separate release paper, which is attached to the pressure sensitive adhesive sheet, is peeled off. If very great care is not taken in the peeling process, the user's hand can come into contact with the pressure sensitive adhesive portion of the pressure sensitive adhesive sheet, and thus the original purpose of preventing secondary bacterial infection cannot be achieved.

SUMMARY OF THE INVENTION

Accordingly, the present invention has been made in order to solve the above-described problems occurring in the art, and it is an object of the present invention to provide a medical dressing comprising an auxiliary release paper which makes it convenient to separate a pressure sensitive adhesive sheet from a release paper and is easily separated from the pressure sensitive adhesive sheet after application to a wound site, thus improving the convenience of use of the dressing, and prevents the contamination of the pressure sensitive adhesive sheet in the process of either separating the pressure sensitive adhesive sheet from the release paper or separating the auxiliary release paper, thus preventing the secondary bacterial infection of a wound site, and is not exposed to the outside so that the dressing has an improved appearance and is convenient to carry and store, and a method for making the dressing.

To achieve the above object, the present invention provides a medical dressing including: a release paper; a pressure sensitive adhesive sheet which is to be applied to a wound site and is attached to one side of the release paper; and a folded auxiliary release paper which is provided between one side of the pressure sensitive adhesive sheet and the release paper and has a V-shaped cross-sectional shape, wherein the auxiliary release paper is formed so as not to be exposed to the outside of the pressure sensitive adhesive sheet, so that the space between the folded portions of the auxiliary release paper is widened when the pressure sensitive adhesive sheet is to be separated from the release paper.

Preferably, embossments may be formed on any one of the folded portions of the auxiliary release paper so that the space between the folded portions can be easily widened.

The present invention also provides a method for making a medical dressing, the method including:

a laminating step of supplying a folded auxiliary release paper having a V-shaped cross-sectional shape to the upper side of a release paper while supplying a raw pressure sensitive adhesive sheet to the upper side of the auxiliary release paper, and passing the supplied auxiliary release paper, release paper and raw pressure sensitive adhesive sheet through pressing rollers to attach them to each other; and a cutting step of cutting the portions of the raw pressure sensitive adhesive sheet and the auxiliary release paper in a laminate, obtained in the laminating step, to a desired shape corresponding to a pressure sensitive adhesive sheet shape, in such a manner that the release paper is not cut while the auxiliary release paper is provided on one side of the cut pressure sensitive adhesive sheet.

BRIEF DESCRIPTION OF THE DRAWINGS

The above and other objects, features and advantages of the present invention will be apparent from the following detailed description of the preferred embodiments of the invention when taken in conjunction with the accompanying drawings, in which.

EXPLANATION ON SYMBOLS

Figure 1:
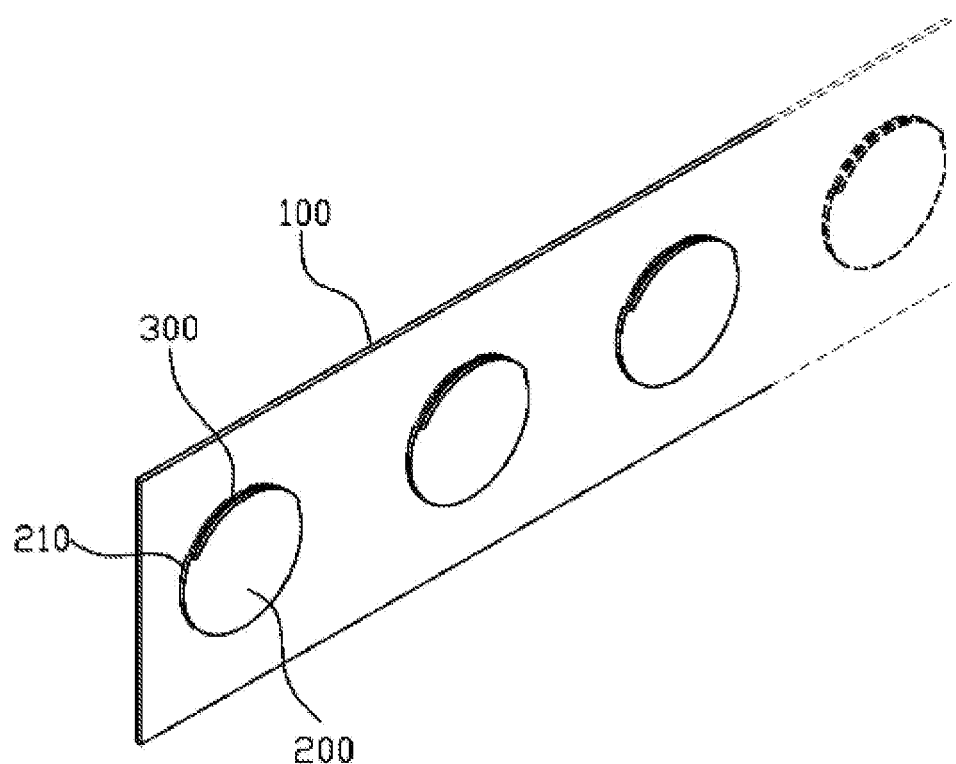
FIG. 1 is a perspective view of a medical dressing according to a preferred embodiment of the present invention.

100: release paper
200, 200': pressure sensitive adhesive sheet
210: pressure sensitive adhesive layer
300: auxiliary release paper
310: first side portion
320: second side portion
330: embossments
S1: laminating step
S2: cutting step
R: pressing roller
P: cutting knife.

DETAILED DESCRIPTION OF THE INVENTION

Hereinafter, the medical dressing of the present invention and a method for making the same will be described in further detail with reference to the accompanying drawings.

Here, the terminology or words used in the specification and the claims of the present invention should not be interpreted as typical meanings or lexical meanings, and they should be interpreted as the meaning and concept conforming to the technological idea of the present invention on the basis of the idea that the inventor can define the concept of the words appropriately in order to illustrate this invention in the best manner.

Therefore, embodiments described herein and configurations illustrated in the drawings are merely the most preferred embodiments of the present invention, and do not represent all of the technical spirits of the present invention. So, it should be understood that various equivalents or modifications substituting for the embodiments could exist at a time point of the application of the present invention.

Figure 2:
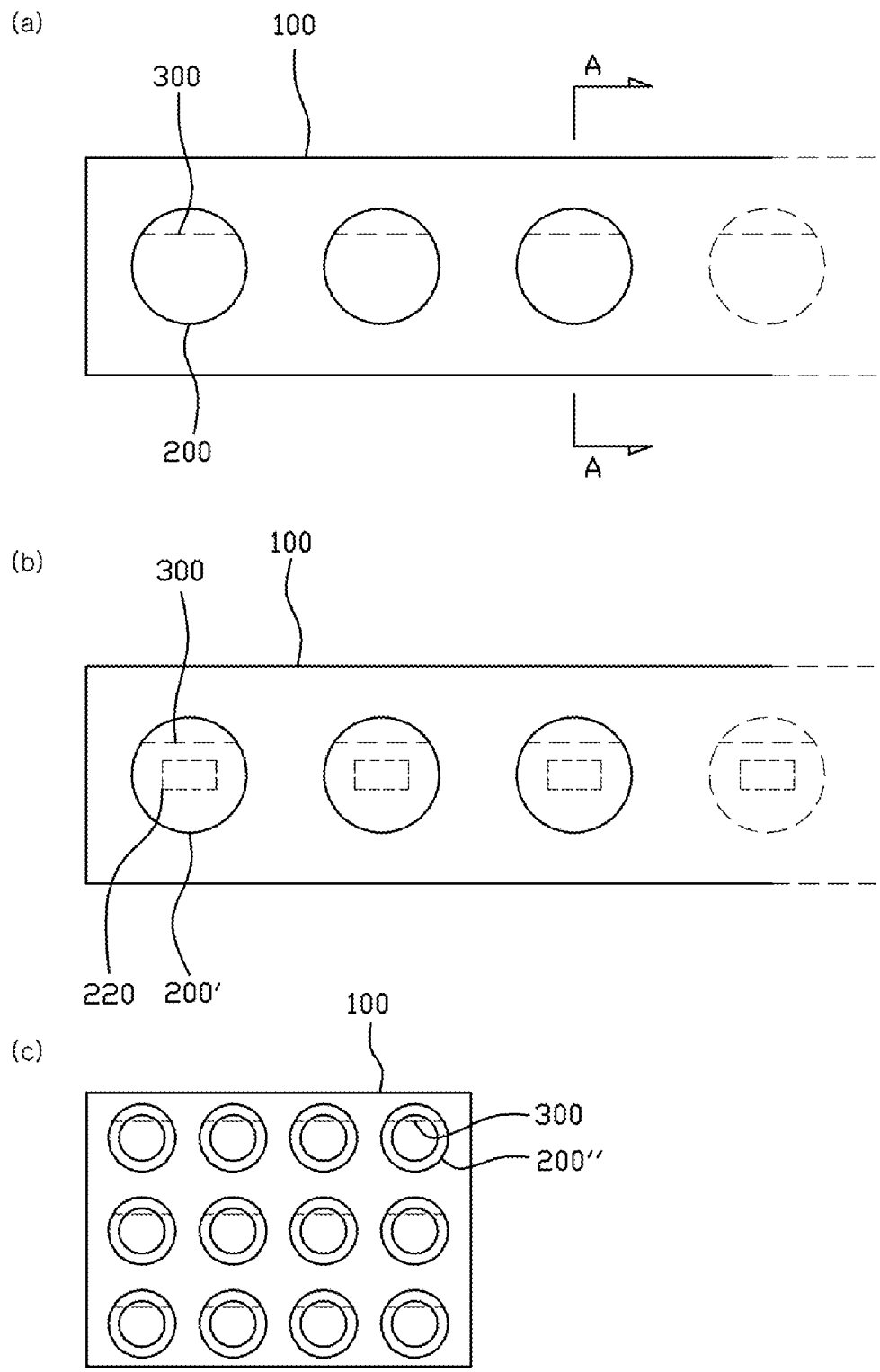
FIG. 2a is a front view of a medical dressing according to a preferred embodiment of the present invention.
FIG. 2b is a front view of a medical dressing according to another embodiment of the present invention.
FIG. 2c is a front view of a medical dressing according to still another embodiment of the present invention.
Figure 3:
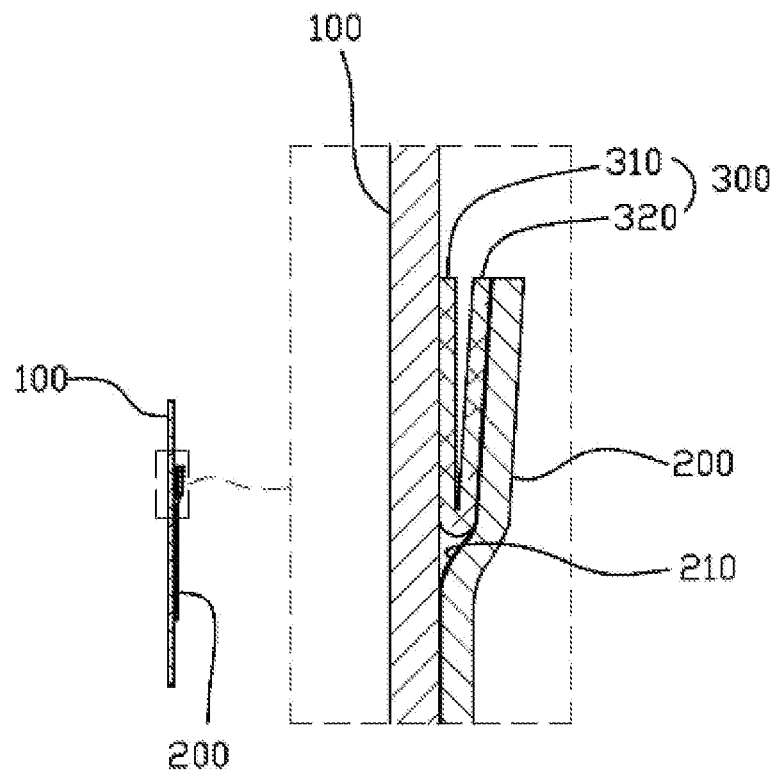
FIG. 3 is a cross-sectional view taken along line A-A of FIG. 2.
Figure 4:
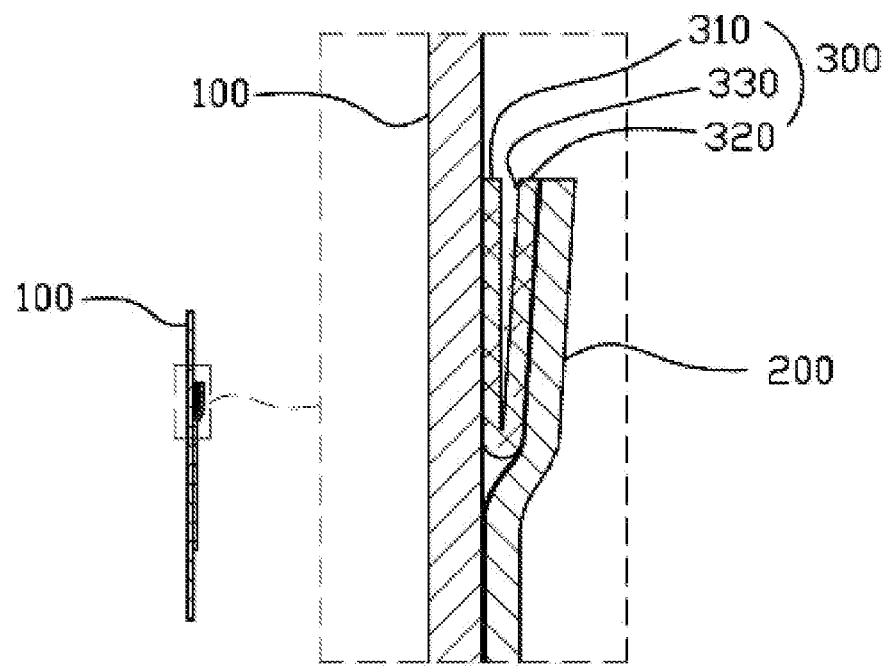
FIG. 4 is a cross-sectional view of a medical dressing according to another embodiment of the present invention.
Figure 5:
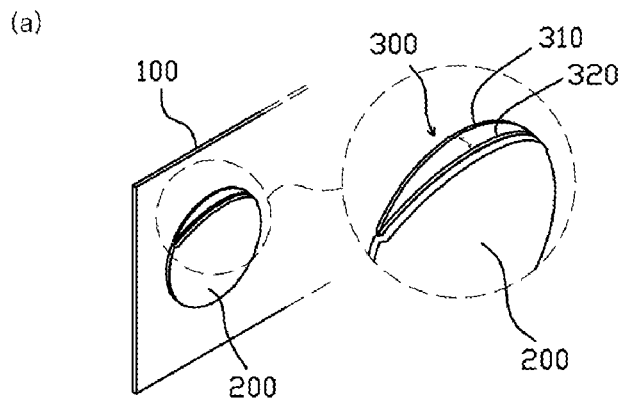
FIGS. 5a to 5c are schematic perspective views showing a method of using a medical dressing according to a preferred embodiment of the present invention.
Figure 5:
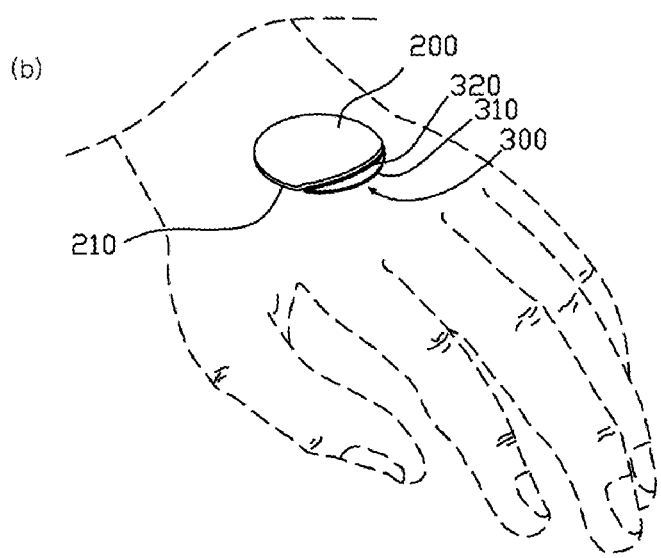
Figure 5:
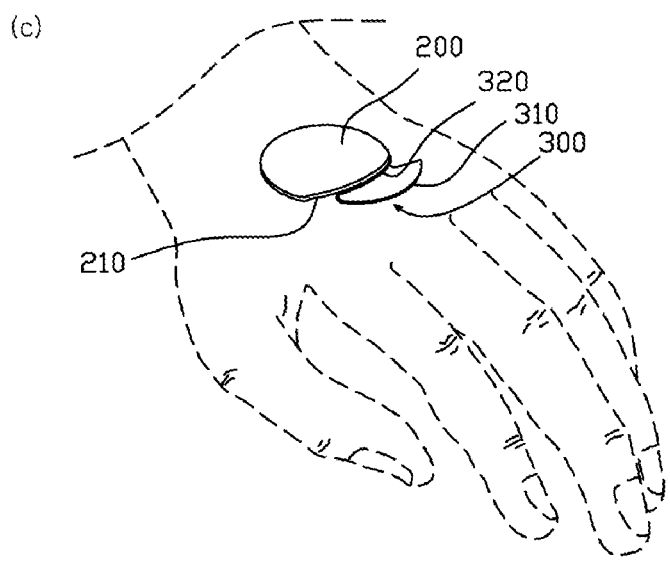
Figure 6:
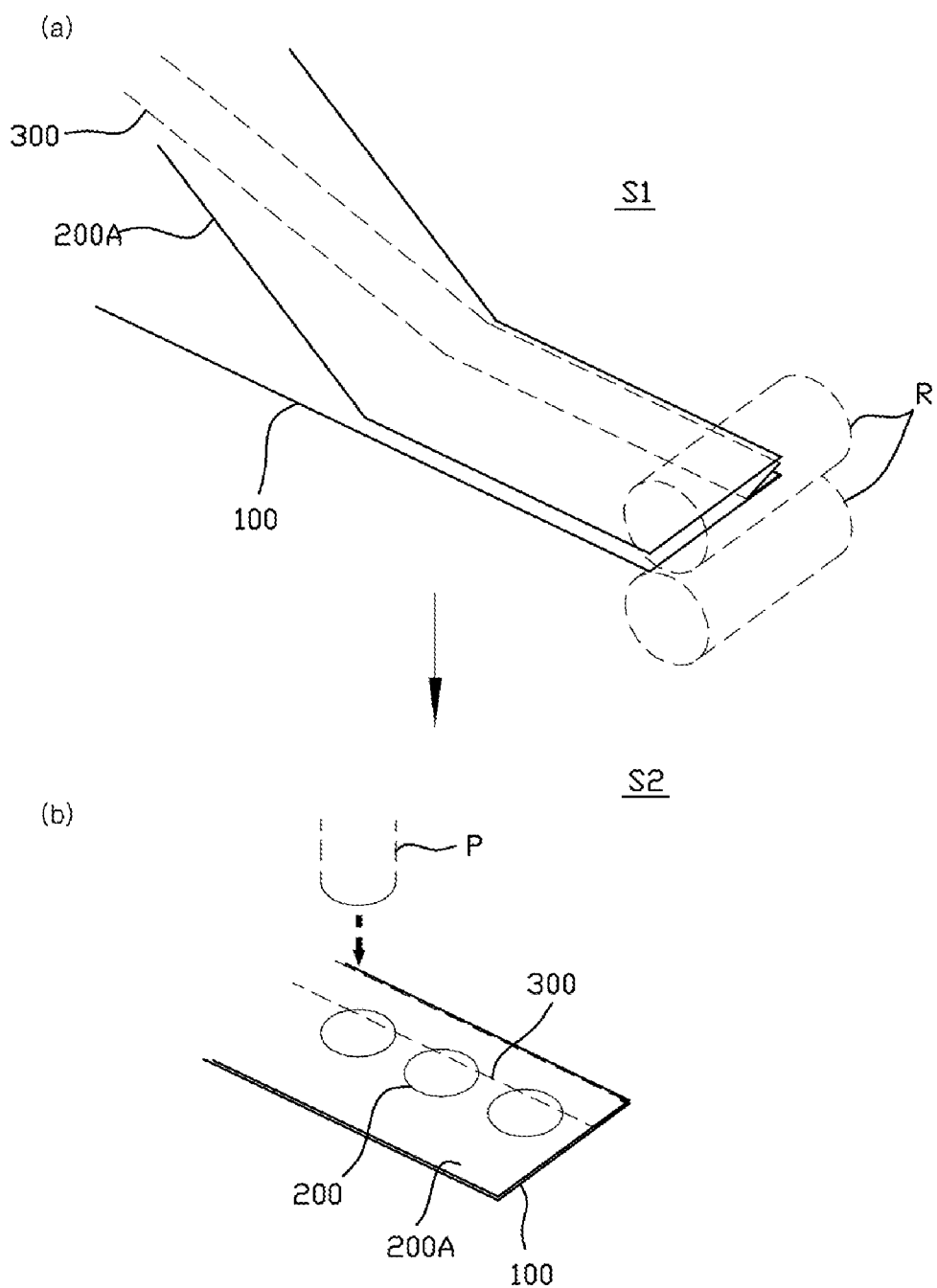
FIGS. 6a and 6b are schematic perspective views showing a method for making a medical dressing according to a preferred embodiment of the present invention.

FIG. 1 is a perspective view of a medical dressing according to a preferred embodiment of the present invention, FIG. 2a is a front view of a medical dressing according to a preferred embodiment of the present invention, FIG. 2b is a front view of a medical dressing according to another embodiment of the present invention, and FIG. 2c is a front view of a medical dressing according to still another embodiment of the present invention, FIG. 3 is a cross-sectional view taken along line A-A of FIG. 2, FIG. 4 is a cross-sectional view of a medical dressing according to another embodiment of the present invention, FIGS. 5a to 5c are schematic perspective views showing a method of using a medical dressing according to a preferred embodiment of the present invention, and FIGS. 6a and 6b are schematic perspective views showing a method for making a medical dressing according to a preferred embodiment of the present invention.

Referring to FIGS. 1 to 3, the medical dressing of the present invention comprises a release paper 100 formed to have a certain length and width, a pressure sensitive adhesive sheet attached to one side of the release paper, and an auxiliary release paper 300 provided between the pressure sensitive adhesive sheet 200 and the release paper 100.

Herein, a smooth coating layer is preferably formed on one side of the release paper 100 so that the pressure sensitive adhesive sheet 200 can be attached and detached.

Also, on the side of the pressure sensitive adhesive sheet 200, which is attached to the release paper 100, a pressure sensitive adhesive layer (i.e., adhesive portion) 210 to be adhered to the release paper 100 is formed. The pressure sensitive adhesive layer 210 is adhered to the affected part of the skin, and the pressure sensitive adhesive sheet 200 may have various shapes according to the consumer's demand.

Meanwhile, the pressure sensitive adhesive sheet 200 may be a hydrocolloid pressure sensitive adhesive sheet, a polyurethane foam pressure sensitive adhesive sheet or the like, which is currently increasingly used. The hydrocolloid pressure sensitive adhesive sheet comprises a hydrophilic hydrocolloid polymer dispersed on a hydrophobic rubbery matrix having a pressure sensitive adhesion strength, and the polyurethane foam pressure sensitive adhesive sheet comprises a mixture of isocyanate, a catalyst, water and the like, dispersed on a hydrophobic rubbery matrix having a pressure sensitive adhesion strength. The hydrocolloid pressure sensitive adhesive sheet or the polyurethane foam pressure sensitive adhesive sheet has a moisture absorption property, shows the abilities to maintain a moist environment and dress wounds, and has excellent adhesive properties. Due to such properties, the hydrocolloid pressure sensitive adhesive sheet is widely used, and thus the detailed description thereof is omitted herein.

According to another embodiment as shown in FIG. 2b, a dressing comprising a pressure sensitive adhesive sheet 200' having a gauze attached thereto may be used. According to still another embodiment as shown in FIG. 2c, a dressing comprising a plurality of hydrocolloid type pressure sensitive adhesive sheets 200" and a thin edge thickness may also be used. This dressing having a thin edge thickness is disclosed in Korean Patent Registration No. 10-0987287, and thus the detailed description thereof will be omitted herein.

The auxiliary release paper 300 is preferably made of a thin material, such as a material having a smooth coating layer formed thereon, like the release paper 100, or a film. The auxiliary release paper 300 has an approximately V-shaped cross-sectional shape, is provided between one side of the pressure sensitive adhesive sheet 200 and the release paper 100, and is composed of a first side portion 310 facing one side of the release paper 100, and a second side portion 320 attached to the back side of the pressure sensitive adhesive sheet 200. As shown in FIG. 3, the auxiliary release paper 300 is preferably configured such that it is not exposed to the outside of the pressure sensitive adhesive sheet 200 (that is, does not protrude from the pressure sensitive adhesive sheet 200). It is to be understood that the auxiliary release paper 300 may have a U-shaped cross-sectional shape in addition to a V-shaped cross-sectional shape.

Because the auxiliary release paper 300 is formed such that it is not exposed to the outside of the pressure sensitive adhesive sheet 200, the dressing has an improved appearance and is convenient to carry or store in a case or the like.

According to another embodiment as shown in FIG. 4, a plurality of small protrusions (i.e., embossments 330) may be formed on at least one of the first side portion 310 and second side portion 320 of the auxiliary release paper 300 so that the space between the first side portion 310 and the second side portion 320 can be easily widened.

Hereinafter, a method of using the medical dressing of the present invention will be described.

FIGS. 5a to 5c are schematic perspective views showing a method of using the medical dressing according to a preferred embodiment of the present invention.

Referring to FIG. 5a, in order to separate the pressure sensitive adhesive sheet 200 from the release paper 100, the space between the folded portions of the auxiliary release paper 300 provided between the pressure sensitive adhesive sheet 200 and the release paper is widened, after which a finger is inserted between the folded portions, and the second side portion 320 of the auxiliary release paper 300 and the surface of the pressure sensitive adhesive sheet 200 are gripped by the fingers and pulled.

Then, as shown in FIG. 5b, the pressure sensitive adhesive sheet 200 is applied to an affected part such as hand. Herein, a portion of the pressure sensitive adhesive sheet 200, to which the auxiliary release paper 300 is not attached, is first applied. Then, as shown in FIG. 5c, the first side portion 310 of the auxiliary release paper 300, which faced one side of the release paper 100, is gripped by fingers, and the auxiliary release paper 300 is completely separated from the pressure sensitive adhesive sheet, after which the surface of the pressure sensitive adhesive sheet 200 is pressed down so that the pressure sensitive adhesive sheet 200 is adhered to the affected part.

As described above, in order to separate the pressure sensitive adhesive sheet 200 from the release paper 100, the space between the folded portions of the auxiliary release paper 300 is widened and the second side portion 320 of the auxiliary release paper 300 and the surface of the pressure sensitive adhesive sheet 200 are gripped by the fingers and pulled. Thus, the contamination of the pressure sensitive adhesive layer 210 during application of the pressure sensitive adhesive sheet 200 to the skin can be prevented. In the process of adhering the pressure sensitive adhesive sheet 200 to the affected part, the first side portion 310 of the auxiliary release paper 300, which is not attached to the pressure sensitive adhesive sheet 200, is gripped by fingers, and the auxiliary release paper 300 is separated from the pressure sensitive adhesive sheet 200. Thus, hand does not come into contact with the pressure sensitive adhesive layer 210 of the pressure sensitive adhesive sheet 200, and thus the contamination of the pressure sensitive adhesive layer 210 can be fundamentally prevented.

Hereinafter, a method for making the medical dressing of the present invention will be briefly described.

FIGS. 6a and 6b are schematic perspective views showing a method for making the medical dressing of the present invention.

Referring to FIGS. 6a and 6b, the method for making the medical dressing comprises a laminating step S1 and a cutting step S2.

In the laminating step S1, the folded auxiliary release paper 300 is supplied to one side of the release paper 100 while a raw pressure sensitive adhesive sheet 200A having the pressure sensitive adhesive layer 210 formed on the lower side thereof is supplied to the upper side of the auxiliary release paper, and the supplied auxiliary release paper, release paper and raw pressure sensitive adhesive sheet are passed through pressing rollers so that they are attached to each other.

Then, the portions of the raw pressure sensitive adhesive sheet 200A and the auxiliary release paper 300 in the laminate are cut to a desired shape (e.g., disc shape) using a cutting knife P in such a manner that the auxiliary release paper 300 is provided on one side of the formed pressure sensitive adhesive sheet 200 while the release paper is not cut. Then, the raw pressure sensitive adhesive sheet 200A and the auxiliary release paper 300, excluding the formed disc-shaped portion, are removed, and thus only the disc-shaped pressure sensitive adhesive sheet 200 and the auxiliary release paper 300 attached to a portion of the back side thereof remain on the release paper 100. In this way, the dressing of the present invention is made.

As described above, according to the present invention, the folded auxiliary release paper having an approximately V-shaped cross-sectional shape is provided between one side of the pressure sensitive adhesive sheet and the release paper, and thus the separation of the pressure sensitive adhesive sheet from the release paper is convenient, and the separation of the auxiliary release paper from the pressure sensitive adhesive sheet after application to a wound site is also easy, indicating that the convenience of use of the medical dressing is improved. In addition, the contamination of the pressure sensitive adhesive sheet in a process of separating the pressure sensitive adhesive sheet from the release paper or separating the auxiliary release paper is prevented, and thus secondary bacterial infection of a wound site is prevented. Furthermore, because the auxiliary release paper is not exposed to the outside of the pressure sensitive adhesive sheet, the medical dressing has an improved appearance and is convenient to carry and store.

While the preferred embodiments of the present invention has been shown and described with reference to the accompanying drawings, they are merely illustrative embodiments, and the invention is not limited to these embodiments. It is to be understood by a person having an ordinary skill in the art that various equivalent modifications and variations of the embodiments can be made without departing from the spirit and scope of the present invention. Therefore, various embodiments of the present invention are merely for reference in defining the scope of the invention, and the true technical scope of the present invention should be defined by the technical spirit of the appended claims.

What is claimed is:

1. A medical dressing comprising:
 a release paper;
 a plurality of pressure sensitive adhesive sheets arranged in regular pattern and attached to one side of the release paper, each of the pressure sensitive adhesive sheets having a predetermined shape and configured to be applied to a treatment site; and
 a plurality of folded auxiliary release papers, each auxiliary release paper positioned between one side of the pressure sensitive adhesive sheet and the release paper and having a symmetrically folded shape with a first side portion and a second side portion at a circumferential side opposite from its folding line, wherein the first and second side portions of each of the folded auxiliary release papers are simultaneously cut to have a shape coincident with the predetermined shape of the pressure sensitive adhesive sheet, such that a space between the first and second side portions of the auxiliary release paper is widened when the pressure sensitive adhesive sheet is to be separated from the release paper.

2. The medical dressing according to claim 1, wherein the release paper has an extended sheet shape, and the plurality of pressure sensitive adhesive sheets are linearly arranged on the release paper.

3. The medical dressing according to claim 2, wherein each of the pressure sensitive adhesive sheets has a circular shape.

4. The medical dressing according to claim 2, further comprising a gauze attached to a central area of each of the pressure sensitive adhesive sheets.

5. The medical dressing according to claim 1, wherein embossments are formed on any one or both surfaces of the first and second side portions of the auxiliary release papers so that the space between the first and second side folded portions can be easily widened.

6. A method for making a medical dressing, the method comprising:
 a laminating step of supplying a folded auxiliary release paper having a V-shaped cross-sectional shape to an upper side of a release paper while supplying a pressure sensitive adhesive sheet to an upper side of the auxiliary release paper, and passing the supplied auxiliary release paper, release paper and pressure sensitive adhesive sheet through pressing rollers to attach them to each other; and
 a cutting step of cutting circumferential areas of the pressure sensitive adhesive sheet and the auxiliary release paper in a laminate, obtained in the laminating step, to a desired shape corresponding to a pressure sensitive adhesive sheet shape, in such a manner that the release paper is not cut while the auxiliary release paper is provided on one side of the cut pressure sensitive adhesive sheet.

* * * * *